(12) United States Patent
Chen et al.

(10) Patent No.: US 7,854,090 B2
(45) Date of Patent: *Dec. 21, 2010

(54) METHOD OF HORMESIS FOR SEAWEED THROUGH IRRADIATION

(75) Inventors: Yean-Chang Chen, Taoyuan (TW); Chia-Chieh Chen, Taoyuan (TW); Kuan-Yin Chen, Taoyuan (TW); Hsueh-Hsuan Liu, Taoyuan (TW); Bin Lin, Taoyuan (TW); Meng-Chou Lee, Taoyuan (TW); Ming-Chao Kuo, Taoyuan (TW); Wen-Song Hwang, Taoyuan (TW); Ying-Kai Fu, Taoyuan (TW); Wuu-Jyh Lin, Taoyuan (TW); Lie-Hang Shen, Taoyuan (TW)

(73) Assignee: Atomic Energy Council-Institute of Nuclear Energy Research, Taoyuan (TW)

( * ) Notice: Subject to any disclaimer, the term of this patent is extended or adjusted under 35 U.S.C. 154(b) by 945 days.

This patent is subject to a terminal disclaimer.

(21) Appl. No.: 11/478,680

(22) Filed: Jul. 3, 2006

(65) Prior Publication Data

US 2010/0236141 A1 Sep. 23, 2010

(51) Int. Cl.
 *A01H 13/00* (2006.01)
(52) U.S. Cl. ............... 47/1.4; 47/58.1 R
(58) Field of Classification Search ............. 47/1.01 R, 47/1.4, 58.1 R, 58.1 LS, 58.1 SE, 59 R, 60
See application file for complete search history.

(56) References Cited

U.S. PATENT DOCUMENTS

| 3,879,890 | A | * | 4/1975 | Chen et al. ............... 47/1.4 |
| 3,982,540 | A | * | 9/1976 | Ross ............... 604/540 |
| 4,417,415 | A | * | 11/1983 | Cysewski et al. ............... 47/1.4 |
| 4,778,731 | A | * | 10/1988 | Kraatz et al. ............... 428/623 |
| 5,585,544 | A | * | 12/1996 | Cheney et al. ............... 800/277 |
| 5,588,254 | A | * | 12/1996 | Adachi et al. ............... 47/57.6 |
| 6,117,815 | A | * | 9/2000 | Makuuchi et al. ............... 504/292 |

FOREIGN PATENT DOCUMENTS

| EP | 1878334 | * | 1/2008 |
| JP | 45-18253 | * | 6/1970 |
| JP | 54-101447 | * | 8/1979 |
| JP | 58-24504 | * | 2/1983 |
| JP | 2002-320426 | * | 11/2002 |

OTHER PUBLICATIONS

Neeraja S. et al., "Gamma-Ray Induced Studies on Rhizoclonium-Hieroglyphicum AG. Kuetz", Indian Botanical Reporter, vol. 8, No. 2, 1989, pp. 107-111.
Wang, Su-Juan et al., "Gamma-Rays Induction of Mutation in Conchocelis of Porphyra Yezonesis", Chinese Journal of Oceanology and Limnology, vol. 18, No. 1, 2000, pp. 47-53.
Hamada J. et al., "Different Cell Inactivation Kinetics of Gamma-Rays and Boron-10 Neutron-Captured Beams on a Green Alga Cylindrocystis-Brebissonii", Annual Reports of the Research Reactor Institute Kyoto University, vol. 24, 1991, pp. 33-41.

* cited by examiner

*Primary Examiner*—David J Parsley

(57) ABSTRACT

Through a low-dose irradiation, a seaweed's growth becomes fast and its production is improved as well. By doing so, a material for biomass energy is provided.

2 Claims, 2 Drawing Sheets

METHOD OF HORMESIS FOR SEAWEED THROUGH IRRADIATION

FIELD OF THE INVENTION

Figure 1:
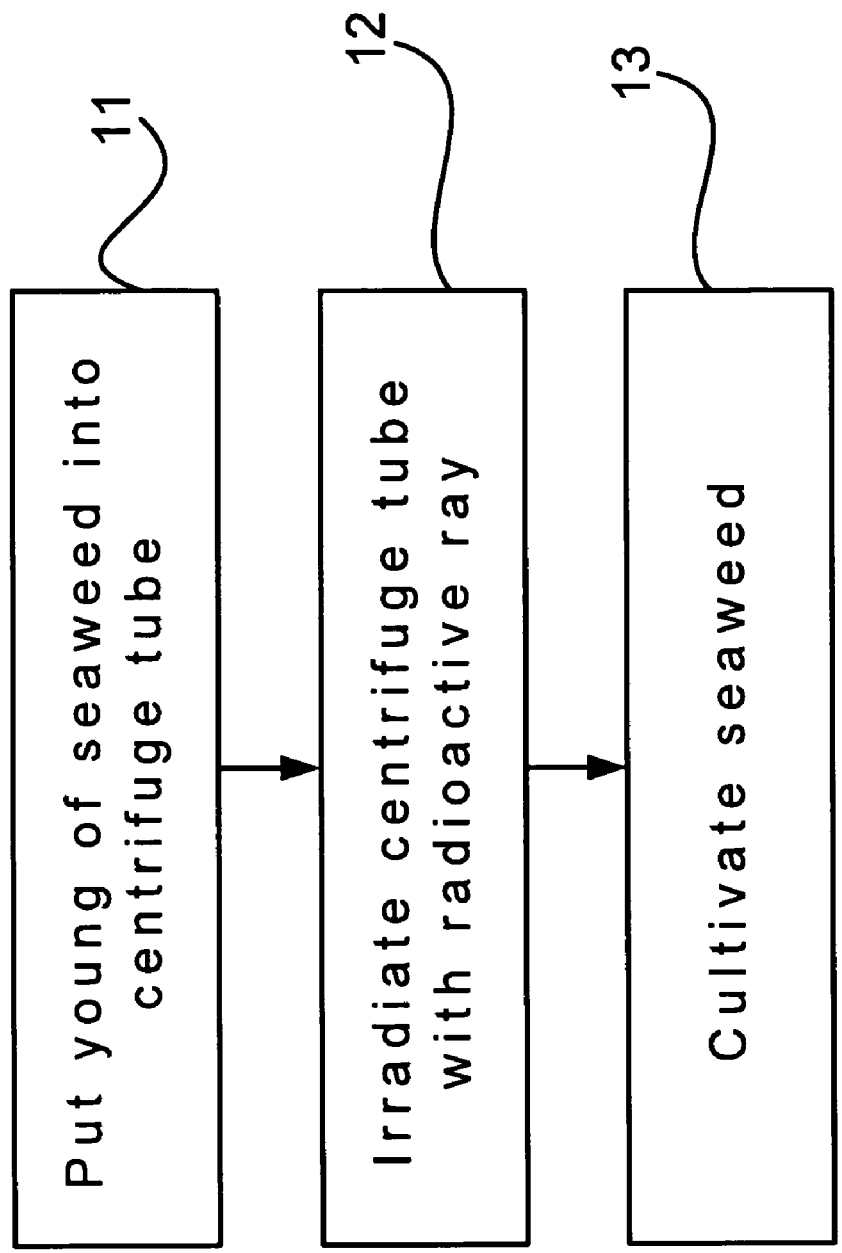

The present invention relates to a method of hormesis; more particularly, relates to irradiating a seaweed with a radioactive ray for obtaining a hormesis to speed up growth and provide a material for biomass energy.

DESCRIPTION OF THE RELATED ARTS

All kinds of energies are essential to our daily lives, no matter in the fields of eating, clothing, living, transporting, educating, entertaining, etc. Following the development in human's society, people are facing great challenges from the environment and the becoming shortage in energy.

Energies used today are mainly petrochemical fuels, such as coal, oil, natural gas, etc. But petrochemical fuels have a certain amount in the world and their forming is slow enough; not to mention the consumption now is so fast with a possibility of a green-house effect to the earth by burning these fuels. Hence, some reports show that these fuels may run out one day. According to Energy. Information Administration of Department of Energy, oil may run out in 40 years; general natural gas in 60 years; coal in 200 years; and nuclear energy of uranium in 70 years. The public is not so conscious about energy saving. Therefore, some must-do's include, in one aspect, changing people's habits on energy usages and educating people the importance of energy saving; and, in another aspect, finding alternative energies and developing renewable energies.

Concerning the expanding needs on energy, developing renewable energies is a matter so urgent that studies on solar energy, terrestrial heat, wind power, tidal energy, etc. all become hits, where biomass energy is one of the most advanced horizon. Biological resources are so abundant on earth. Under an estimation, the earth produces about 172.5 billions of biomass per year through photosynthesis. As a renewable energy, the energy these biomass contain is about 10 to 20 times of the energy the whole world consumes. Yet, we utilize only 1 to 3 percents of the energy. Hence, a best solution for energy may lies in effectively utilizing the biomass energy. Regarding the seaweed as a material for biomass energy, seaweed production has to be maintained at a certain amount to make seaweed an alternative energy to oil. But most seaweeds grow along sea shores on the rocks, so limited owing the natural environment. Hence, the prior arts do not fulfill users' requests on actual use.

SUMMARY OF THE INVENTION

The main purpose of the present invention is to irradiate a seaweed with a low-dose radioactive ray for obtaining a hormesis to speed up growth and provide a material for biomass energy To achieve the above purpose, the present invention is a method of hormesis for seaweed through irradiation, comprising steps of (a) obtaining at least one young of seaweed to be put into a centrifuge tube having a seaweed cultivation liquid;

(b) irradiating the centrifuge tube with a gamma ray of cobalt-60 having a dose between 5 grays (Gy) and 100 Gy to obtain a hormesis; and (c) moving the young of seaweed from the centrifuge tube to a taper bottle to be put into a plant cultivation cabinet for cultivation.

Accordingly, a novel method of hormesis for seaweed through irradiation is obtained.

BRIEF DESCRIPTIONS OF THE DRAWINGS

Figure 2:
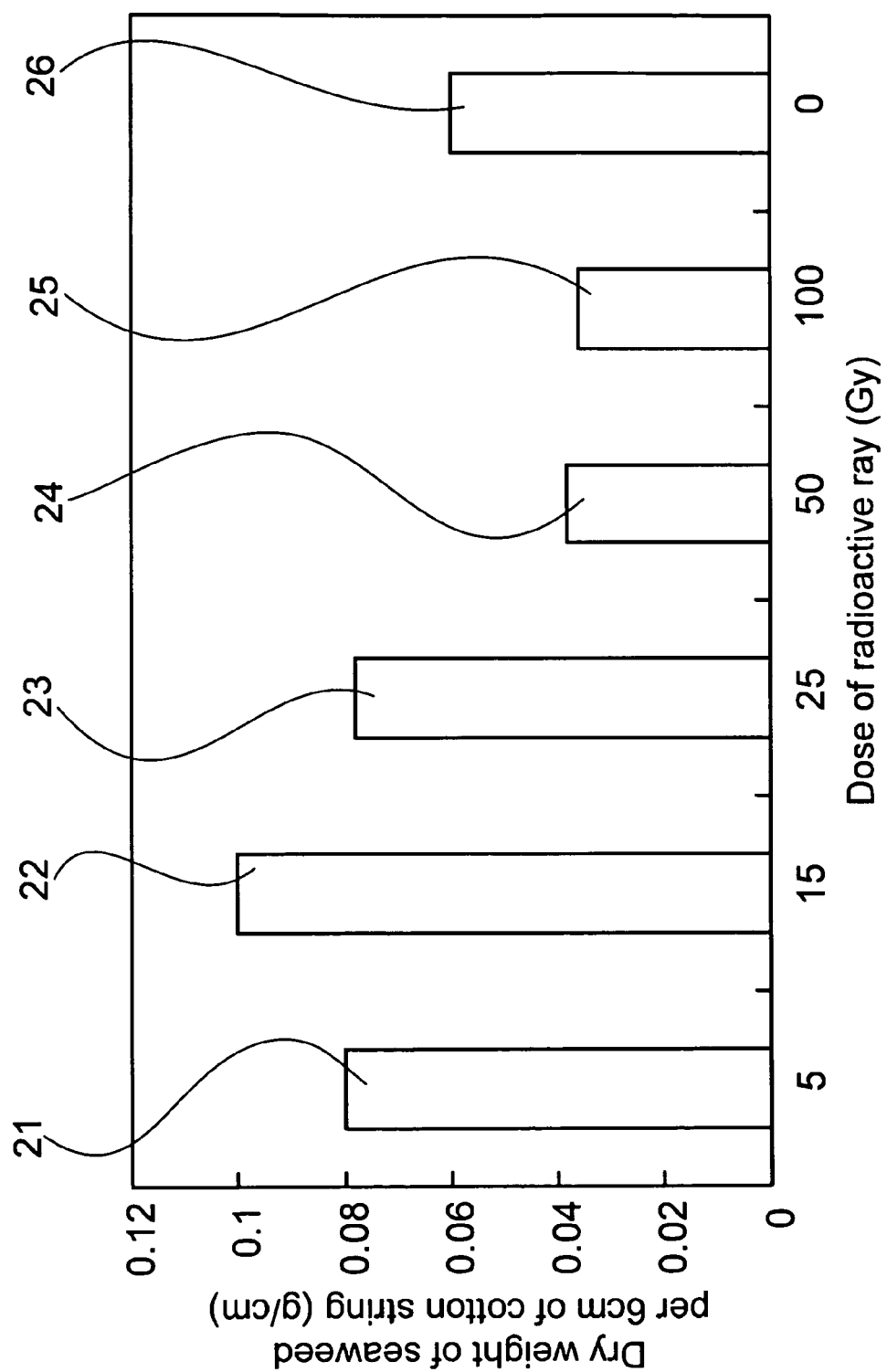

The present invention will be better understood from the following detailed description of the preferred embodiment according to the present invention, taken in conjunction with the accompanying drawings, in which FIG. 1 is a view showing a flow chart of the preferred embodiment according to the present invention; and FIG. 2 is a view showing the relationship between the dose of the radioactive rays and the dry weight of the seaweed.

DESCRIPTION OF THE PREFERRED EMBODIMENT

The following description of the preferred embodiment is provided to understand the features and the structures of the present invention.

Please refer to FIG. 1, which is a view showing a flow chart of the preferred embodiment according to the present invention. As shown in the figure, the present invention is a method of hormesis for seaweed through irradiation, where seaweed is irradiated with a radioactive ray for a hormesis to grow fast and improve production. The method comprises the following steps:

(a) Putting at least one young of seaweed into a centrifuge tube 11: At least one young of seaweed is put into a centrifuge tube having 40 milliliters (ml) of a seaweed cultivation liquid. Therein, at least one young of seaweed is obtained at first by sprouting a germ cell adhered to a seaweed adherence device on a cotton string, where the young of seaweed has a length between 1 and 1.5 mm; and, the cotton string having the young of seaweed is cut to obtain a length between 5 centimeters (cm) and 7 cm to be put into a centrifuge tube having 40 ml of a seaweed cultivation liquid, where the seaweed cultivation liquid is obtained from a sterilized seawater having a salinity of 3.5 percents (%) and being added with 1 ml of a saturated germanium oxide solution per liter.

(b) Irradiating the centrifuge tube with a radioactive ray 12: The centrifuge tube having the young of seaweed is irradiated in water by a gamma ray of cobalt-60 ($Co^{60}$) having a dose between 5 grays (Gy) to 100 Gy.

(c) Cultivating the seaweed 13: Then, the young of seaweed are moved from the centrifuge tube to a taper bottle containing the seaweed cultivation liquid; and the taper bottle is put into a plant cultivation cabinet for a cultivation. Therein, the young of seaweed irradiated by the gamma ray are moved to a taper bottle at first; then the taper bottle is put into a plant cultivation cabinet to cultivate the seaweed under an environment of a temperature between 20 Celsius degrees (° C.) and 30° C., a luminous intensity between 145 and 155 $\mu Em^{-2}s^{-1}$ and a photoperiod of 12/12 (light/dark).

In the above steps, at least one young of seaweed is irradiated by $Co^{60}$ for hormesis to speed up growth of the seaweed and improve a production. Moreover, since the seaweed is a material for biomass energy, the present invention accelerates the growth of the seaweed and improves the production so that material for biomass energy is provided.

Taking sea lettuce as an example, the present invention comprises the following steps:

(a) At least one young of sea lettuce is put into a centrifuge tube having 40 ml of a seaweed cultivation liquid, where at least one young of sea lettuce is obtained at first by sprouting germ cells cohered to an adherence device for sea lettuce on a cotton string; and then the cotton string having the young of sea lettuce is cut to obtain 6 cm of the cotton string to be put into a centrifuge tube having 40 ml of a seaweed cultivation liquid obtained from a sterilized seawater having a salinity of 3.5% and being added with 1 ml of a saturated germanium oxide solution per liter.

(b) The centrifuge tube having the young of sea lettuce is irradiated in water by a gamma ray of $Co^{60}$ with a dose of 15 Gy so that the sea lettuce obtains a hormesis through the irradiation.

(c) Then, the young of sea lettuce is moved from the centrifuge tube to a taper bottle containing a seaweed cultivation liquid; and the taper bottle is put into a plant cultivation cabinet to cultivate the sea lettuce under an environment of a temperature of 24° C., and a luminous intensity of $\mu Em^{-2}s^{-1}$ and a photoperiod.

Please refer to FIG. 2, which is a view showing a relationship between dose of a radioactive ray and dry weight of a seaweed. As shown in the figure, at least one young of sea lettuce is obtained to be put into each centrifuge tube. And each centrifuge tube is irradiated by a radioactive ray having a various dose; then the young of sea lettuce is moved from the centrifuge tube to a taper bottle having 6 cm of a cotton string; and then the taper bottle is put into a plant cultivation cabinet for a cultivation for a period of time. After the period of time, the cotton string cohered with the sea lettuce is taken out to be dried. After removing the cotton string, a dry weight of the sea lettuce is measured. Therein, a first vertical bar 21 is obtained after a 5 Gy of irradiation of a radioactive ray and a first young of the sea lettuce after the irradiation has a dry weight of 0.08 grams per centimeter (g/cm); a second vertical bar 22 obtained after a 15 Gy of irradiation and a second young of the sea lettuce a dry weight of 0.1 g/cm; a third vertical bar 23 after a 25 Gy of irradiation and a third young of the sea lettuce a dry weight of 0.078 g/cm; a fourth vertical bar 24 after a 50 Gy of irradiation and a fourth young of the sea lettuce a dry weight of 0.038 g/cm; a fifth vertical bar 25 after a 100 Gy of irradiation and a fifth young of the sea lettuce a dry weight of 0.035 g/cm; and a sixth vertical bar 25 with no irradiation and a sixth young of the sea lettuce a dry weight of 0.06 g/cm. According to the above results, after growing through an irradiation of the radioactive ray with a dose between 5 Gy to 25 Gy, the youngs of sea lettuce obtained have dry weights greater than the young of sea lettuce growing through no irradiation. And, the young of sea lettuce growing through the irradiation with a dose of 15 Gy has the heaviest weight.

To sum up, the present invention is a method of hormesis for seaweed through irradiation, where an irradiated seaweed obtains a hormesis for rapid growth so that production is improved and a material for biomass energy is provided.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of hormesis for sea lettuce through irradiation, comprising steps of:
    (a) obtaining at least one immature sea lettuce by sprouting a germ cell and placing said immature sea lettuce into a centrifuge tube having a seaweed cultivation liquid;
    (b) irradiating said centrifuge tube with a gamma ray having a dose from 5 Gy to 25 Gy to said at least one immature sea lettuce;
    (c) moving said at least one immature sea lettuce from said centrifuge tube to a taper bottle containing a seaweed cultivation liquid and then locating said taper bottle into a plant cultivation cabinet to cultivate said sea lettuce,
    wherein said cultivating in step (c) has an environment of a temperature between 20 Celsius degrees (° C.) and 30° C., a luminous intensity between 145 $\mu Em^{-2}s^{-1}$ and 155 $\mu Em^{-2}s^{-1}$ and a photoperiod,
    wherein said seaweed cultivation liquid is obtained from a seawater;
    wherein said seawater has a salinity of 3.5%; and
    wherein 1 milliliter (ml) of saturated germanium oxide solution is added into said seawater per liter.

2. The method according to claim 1, wherein said centrifuge tube has a volume of 50 ml; and
    wherein said centrifuge tube contains 40 ml of said seaweed cultivation liquid.

* * * * *